United States Patent
Lewellen et al.

[11] Patent Number: 6,010,391
[45] Date of Patent: Jan. 4, 2000

[54] CRYOGENIC POLISHING METHOD FOR SOFT ACRYLIC ARTICLES

[75] Inventors: Kevin Lewellen, Arlington; John W. Sheets, Jr., Fort Worth, both of Tex.

[73] Assignee: Alcon Laboratories, Inc., Fort Worth, Tex.

[21] Appl. No.: 08/962,604

[22] Filed: Oct. 31, 1997

Related U.S. Application Data

[60] Provisional application No. 60/029,969, Nov. 1, 1996.
[51] Int. Cl.$^7$ .............................. B24B 1/00; B24B 31/00
[52] U.S. Cl. ................................ 451/35; 451/36; 451/43; 451/328
[58] Field of Search .................................. 451/36, 35, 43, 451/328, 330

[56] References Cited

U.S. PATENT DOCUMENTS

| | | |
|---|---|---|
| 2,554,701 | 3/1951 | Hackett et al. . |
| 3,535,159 | 10/1970 | Shiro . |
| 3,874,124 | 4/1975 | Morgan et al. . |
| 3,997,358 | 12/1976 | Taylor . |
| 4,257,196 | 3/1981 | Walther et al. ........................... 451/35 |
| 4,580,371 | 4/1986 | Akhavi . |
| 4,796,388 | 1/1989 | Steckis . |
| 5,133,159 | 7/1992 | Nelson ........................................ 451/32 |
| 5,290,892 | 3/1994 | Namdaran et al. . |
| 5,429,838 | 7/1995 | Mansson et al. . |

FOREIGN PATENT DOCUMENTS

| | | |
|---|---|---|
| 169439 | 6/1988 | Japan . |
| WO 93/06967 | 4/1993 | WIPO . |
| WO 98/19825 | 5/1998 | WIPO . |

*Primary Examiner*—David A. Scherbel
*Assistant Examiner*—Shantese McDonald
*Attorney, Agent, or Firm*—Patrick M. Ryan

[57] ABSTRACT

A method for polishing articles comprising soft acrylic materials is disclosed. The method includes a cryogenic polishing step and a cleaning step. In the polishing step, a receptacle is charged with polishing beads of various sizes, sodium bicarbonate, a swelling agent and the articles to be polished, for a period of time and at a rotation speed sufficient to remove surface irregularities. Following the polishing step, a receptacle is charged with (a) a cleaning slurry comprising cleaning beads of various sizes and (i) sodium hydroxide and water or (ii) alumina, a surfactant and a solvent and (b) the articles to be cleaned, for a period of time and at a rotation speed sufficient to clean the surface of the polished articles. Agitation is preferably accomplished by a tumbling machine.

18 Claims, No Drawings

CRYOGENIC POLISHING METHOD FOR SOFT ACRYLIC ARTICLES

This application claims priority from co-pending U.S. Provisional Pat. application Ser. No. 60/029,969 filed Nov. 1, 1996.

BACKGROUND OF THE INVENTION

1. Field of the Invention

The present invention relates to methods of manufacturing products comprising acrylic materials. In particular, this invention relates to methods for polishing soft acrylic articles to remove rough surfaces and tool or machining marks.

2. Description of Related Art

Soft acrylic materials are used in the manufacture of a wide variety of products. Because soft acrylic materials are generally compatible with biological tissues and fluids, they can be particularly useful in making products for biomedical applications. Examples of such soft acrylic products include soft contact lenses and soft prosthetic implants, such as intracorneal and intraocular lenses, corneal inlays used during refractive surgery, and intracapsular rings used to support the natural lens capsule during ophthalmic surgery.

A highly polished finish, free of sharp edges or surface irregularities, is required in many biomedical applications. Implantable products, such as intraocular lenses, are in direct contact with body tissues and the tearing or abrading of tissue by rough surfaces could result in rupture of blood vessels, irritation or other trauma to the tissue. Even minute irregularities can cause irritation of body tissues. This is a particularly serious problem with contact lenses and portions of intraocular lenses that contact the eye, where the tissue is extremely sensitive.

The use of soft acrylic materials for intraocular lenses is a relatively new development. Intraocular lenses formed of soft acrylic material are advantageous in that they can be folded and inserted through smaller incisions in the cornea than previously possible, resulting in fewer post-operative complications. Rough edges resulting from the cutting of lens blanks or flashing generated during molding can cause intraocular irritation.

In addition, soft contact lenses require a highly polished finish to prevent irritation of the interior of the eyelid and corneal epithelium. The eye is extremely sensitive to imperfections in contact lenses, and even slight ridges resulting from the molding process can produce irritation and discomfort. Expensive molding procedures or individual hand-grinding techniques may be used to provide the desired finish for these lenses.

Mechanical devices utilizing smooth, frictionless movement also require highly polished, smooth surfaces of their soft acrylic products. Obtaining such a highly polished, smoothly-finished soft acrylic article is often difficult as these products are manufactured by curing acrylic material in molds, wherein even the most precise dies result in some flashing and/or irregular edges. The products may be trimmed and polished, but these finishing procedures are generally done by hand, and are both time consuming and expensive, as well as imprecise, so that they do not result in the totally smooth or regular surface required. Further, many of these articles, particularly those for biomedical applications, are relatively small, and/or irregularly shaped, causing difficulties in obtaining the desired finish, and/or clarity.

For silicone materials, such as silicone rubbers and silicone elastomers, tumble polishing processes are known. See, for example, U.S. Pat. No. 5,133,159. However, the tumble polishing methods known for articles made from silicone materials are not adequately applicable to articles made from soft acrylic materials. The removal of imperfections from small and irregularly shaped soft acrylic products is an unsolved problem in the art. It would be of great utility to provide a simple, economic, and effective method for polishing and/or clarifying soft acrylic articles for industrial, medical, and mechanical purposes.

SUMMARY OF THE INVENTION

The present invention provides methods for polishing articles comprising soft acrylic materials. The methods comprise two steps: a cryogenic polishing step and a cleaning step. The polishing step comprises charging a receptacle with a polishing slurry and the articles to be polished, and agitating the receptacle at cryogenic conditions for a period of time and at a speed sufficient to remove surface irregularities from the articles. The polishing slurry comprises polishing beads, sodium bicarbonate and a swelling agent.

After polishing, the articles may contain a surface film or residue causing a hazy appearance. This frost or haze is removed in the cleaning step. The cleaning step comprises charging a receptacle with a cleaning slurry and the articles to be cleaned, and agitating the receptacle for a period of time and at a speed sufficient to clean the surface of the polished articles. The cleaning slurry comprises cleaning beads, and either i) sodium hydroxide and water, or ii) a surfactant, alumina polishing powder, and a solvent.

Examples of articles which may be polished according to the methods of the present invention include one-piece intraocular lenses, intraocular lens haptics, intraocular lens optics, intracapsular rings, corneal inlays, intracorneal lenses, and contact lenses.

DETAILED DESCRIPTION OF THE INVENTION

The present invention provides methods for polishing articles comprising soft acrylic materials. As used herein, "soft acrylic material" means materials comprising polymers or copolymers of acrylic acid, methacrylic acid, esters of these acids, or acrylonitrile, wherein the polymers or copolymers have a glass transition temperature ($T_g$) of about 35° C. or less, and a Shore A Hardness value of about 90 or less. Preferably the soft acrylic materials have a $T_g$ of about 25° C. or less, and most preferably 20° C. or less. The soft acrylic materials preferably have a Shore A Hardness value of about 60 or less, and most preferably about 45 or less.

Examples of soft acrylic materials suitable for making foldable intraocular lenses include but are not limited to (i) the acrylic material made from copolymerizing about 65 wt. % 2-phenylethyl acrylate, about 30 wt. % 2-phenylethyl methacrylate, an ultraviolet absorber and a cross-linking agent, and (ii) the acrylic material made from copolymerizing about 80 wt. % 2-phenylethyl acrylate, about 15 wt. % 2-hydroxyethyl methacrylate, an ultraviolet absorber and a cross-linking agent. These and other suitable soft acrylic materials are described in U.S. Pat. No. 5,290,892 and in co-pending, commonly-assigned U.S. Pat. application Ser. No. 08/739,245. Other examples of soft acrylic materials include, but are not limited to, those disclosed in U.S. Pat. No. 5,331,073.

As used herein, the "Preferred Acrylic Material" means the soft acrylic material obtained by copolymerizing about 65 wt. % 2-phenylethyl acrylate, about 30 wt. % 2-phenylethyl methacrylate, about 1.8 wt. % o-methallyl Tinuvin P and 3.2 wt. % 1,4-butanediol diacrylate, using 1.8 wt. % Perkadox 16 as an initiator.

The present methods comprise a polishing step and a cleaning step. The polishing step is conducted under cryogenic conditions, typically at temperatures of about 0° C. or less, and preferably at about −10° C. or less. In the polishing step, a receptacle is charged with a polishing slurry and the articles to be polished. The receptacle may be various sizes and shapes, and may be formed of glass, polycarbonate, or other suitable material. The receptacle is preferably a square plastic container, such as a 1 liter Nalgene® square plastic jar.

The polishing slurry ingredients comprise a mixture of polishing beads, sodium bicarbonate and one or more swelling agents. As one skilled in the art will appreciate, however, the exact composition of the polishing slurry will vary depending on a variety of factors, such as the identity of the acrylic material and the size and shape of the article to be polished. Preferably, the polishing beads are glass beads, which are relatively inexpensive and readily commercially available, but may be solid or filled beads formed of any suitable material. Commercially available glass beads are available in a variety of sizes, for example 0.3, 0.5, 1 and 2 mm sizes. The glass beads contained in the polishing slurry have preferably been preconditioned so that they are not in a raw state; that is, they have preferably been slightly worn or conditioned so that they are less likely to harm the surface of the lens. One convenient way to condition the beads is to first employ them in the NaOH/$H_2O$ cleaning step described below. After their rough surfaces have been slightly worm, the beads may be utilized in the polishing step.

The necessary number and size distribution of polishing beads will vary with the number and size of the articles to be polished, but a suitable selection can be easily determined without undue experimentation. Generally, a mixture of polishing beads of different sizes is preferred. In the case of the Preferred Acrylic Material, for example, the polishing slurry would comprise 0.5 mm, 1.0 mm and 2.0 mm glass beads in a 1:2:1 ratio. For example, the polishing beads added to a 1 liter receptacle would comprise approximately 1000 g of polishing beads as follows: about 250 g of 0.5 mm glass beads, about 500 g of 1.0 mm glass beads, and about 250 g of 2.0 mm glass beads.

The polishing slurry also contains sodium bicarbonate as a polishing agent. The optimum amount of the sodium bicarbonate will depend on other process parameters, including the identity of the soft acrylic material. In general, however, the polishing slurry contained in a 1 liter receptacle will require a minimum of approximately 0.25% sodium bicarbonate to solvent to achieve satisfactory results, regardless of the size and shape of the articles to be polished. Increasing the amount of sodium bicarbonate seems to increase the efficiency of the polishing slurry, up to a maximum of about 2.5% (sodium bicarbonate to swelling agent, w/w basis). Higher concentrations of sodium bicarbonate may result in damage to the article(s) being processed and do not appear to provide any significant improvement in polishing efficiency or results. In the case of the Preferred Acrylic Material, the polishing slurry contains about 1.25% sodium bicarbonate to swelling agent (w/w).

In addition to polishing beads and sodium bicarbonate, the polishing slurry also comprises one or more swelling agents. The swelling agent ingredient slightly swells the article to be polished, making its surface(s) more brittle, thereby facilitating and improving the polishing results. In addition to slightly swelling the article to be polished, the swelling agent also serves as the medium for the sodium bicarbonate and polishing beads. Any agent capable of swelling the article to be polished without irreversibly damaging it will be suitable. In general, two categories of swelling agents can be identified: solvents and polymer solutions. Solvents are generally preferred over polymer solutions because they are simpler to use and require less processing steps.

Suitable solvents include, but are not limited to, alcohols, aliphatic hydrocarbons, chlorinated solvents, and aromatic hydrocarbons. Examples of suitable alcohol solvents include short chain alcohols (approximately 10 total carbon atoms or less), such as methanol, ethanol, and isopropanol. Examples of suitable aliphatic hydrocarbon solvents include pentane, hexane, heptane and mineral spirits. Examples of suitable chlorinated solvents include methylene chloride and trichloromethane. Examples of suitable aromatic hydrocarbon solvents include benzene and toluene. Preferred solvents include mineral spirits with flash points of about 90–145° F., such as the mineral spirits fraction known as stoddard solvent.

Suitable polymer solutions for use as swelling agents include liquid polymers or polymer solutions which can be imbibed into or impregnate the soft acrylic materials to be polished, but which can be removed by a solvent extraction process following the polishing step. For example, a polymer solution can be prepared by dissolving polymethylmethacrylate in acetone. The articles to be polished can then be soaked in the solution for a time sufficient to cause the articles to swell and become embrittled. The embrittled articles can then be polished, after which the impregnated polymethylmethacrylate can be removed by extraction with acetone. Other suitable polymer solutions include solutions of other acrylic polymers including, but not limited to, homopolymers of monomers contained in the soft acrylic material to be polished. Mixed polymers may also be used. The fundamental requirement is that the polymer be capable of impregnating the soft acrylic material and that the polymer's glass transition temperature be greater than the polishing process temperature and the glass transition temperature of the soft acrylic material. Examples of polymers for use as swelling agents include poly(phenylethyl methacrylate) and poly(phenyl methacrylate). In some cases where the swelling agent is chosen to be a homopolymer, the homopolymer may be a liquid at the polishing process temperature, in which case no solvent is needed until the homopolymer is extracted from the polished article. In such a case, the liquid homopolymers are nevertheless referred to as "polymer solutions" for purposes of the present invention. In other cases, the chosen polymeric swelling agent will need to be dissolved in a solvent which is capable of dissolving the swelling agent but not the article to be polished in order to for a solution of the swelling agent.

Just as in the case of determining the optimum amount of sodium bicarbonate to include in the polishing slurry, the identity and amount of swelling agent which should be included in the polishing slurry will depend upon the identity of the chosen soft acrylic material. For certain acrylic materials and polishing conditions, swelling agents having specific boiling point ranges or glass transition temperatures will function better than others in the polishing slurry. In the case of the Preferred Acrylic Material, the preferred swelling agent is a commercially available mineral spirits fraction known as "stoddard solvent." Other mineral spirit fractions or other swelling agents may be more suitable for soft acrylic materials other than the Preferred Acrylic Material. In general, a suitable amount of swelling agent is that amount which is sufficient to cover the standing volume of polishing beads contained in the polishing slurry. Thus, in a one liter receptacle containing approximately 1000 g of glass polishing beads, the preferred polishing slurry for the Preferred Acrylic Material comprises about 250 mL of stoddard solvent as the mineral spirits ingredient.

The polishing slurry is preferably formulated in the receptacle in the absence of the acrylic articles that are to be polished. For convenience, the polishing slurry may be prepared in two steps. First, the receptacle containing the polishing beads and sodium bicarbonate is vacuum dried to remove any moisture. It is very desirable to eliminate moisture from the receptacle and polishing slurry. For example, the receptacle containing the polishing beads and sodium bicarbonate may be heated to about 50° C. at ≧50 mm Hg for approximately 24 hours. After the moisture elimination step, the chosen swelling agent ingredient is added to the receptacle and then the polishing slurry is mixed under cryogenic conditions (i.e., about 0° C. or less) before the articles to be polished are added. For example, in the case of a 1 liter receptacle and the polishing slurry for the Preferred Acrylic Material, the complete polishing slurry is tumbled for a short time (approximately 1 hour) at about −10° C. before the articles to be polished are added.

Once the articles to be polished are added to the mixed, pre-chilled polishing slurry, the receptacle is agitated for a time and at a speed sufficient to remove any rough spots, sharp edges, and any tool or machining marks from the articles' surfaces. Agitation is preferably accomplished by placing the receptacle on a rotational apparatus such as a commercially available tumbling machine (e.g., Model 3BAR from Topline Mfg. Co., Fullerton, Ca.). The optimal time and rotation speed will vary with the batch size, identity of the soft acrylic material, the size and shape of the articles to be polished, etc. When the methods of the present invention are used to polish intraocular lenses, a typical batch size will be on the order of 50–100 lenses for a 1 liter receptacle. In the case of the Preferred Acrylic Material, excellent polishing results are obtained when the article is tumble-polished for approximately 1–3 days, with the rotation speed of the receptacle being approximately 80 rpm.

After the polishing step, the articles are separated from the polishing beads by emptying the contents of the polishing jar into a sieve stack so that the swelling agent is drained away. The articles are then rinsed by flushing with either fresh solvent or D.I. water to separate the lenses from the beads. The polished articles will appear very smooth, but may appear hazy or frosty, as if there is a residue on the surface of the polished articles. This frosty appearance is removed in a cleaning step.

After the articles are polished but before they are subjected to the cleaning step, it may be advantageous to reduce or eliminate any residual swelling agent from the articles' surfaces in the event that the chosen cleaning slurry contains water and sodium hydroxide. This can be accomplished by briefly cleaning the articles in a commercially available ultrasonic cleaner. Cleaning solutions suitable for use in ultrasonic cleaners generally include solvents, detergents, water and mixtures thereof. The exact composition of the cleaning solution is not critical, though it may be desirable to adjust the composition's ingredients based upon the identity of the chosen solvent. In the case where the swelling agent is chosen to be stoddard solvent, a suitable stock ultrasonic cleaning solution comprises a mixture of water, 2-butoxyethanol, Micros® detergent, and ammonium hydroxide.

Following ultrasonic cleaning, if any, the polished articles are cleaned in an agitating receptacle containing a cleaning slurry comprising cleaning beads and either i) sodium hydroxide in water, or, preferably, ii) alumina polishing powder, a surfactant and a solvent. If the cleaning slurry comprises water, the water is preferably deionized water. If the cleaning slurry comprises alumina, the solvent is preferably the same as any solvent utilized in the polishing slurry. As in the polishing step above, the agitation is preferably achieved by means of a rotational machine. The receptacle is preferably a 1 liter round glass jar with a glass lid, though any receptacle having a shape in which the articles to be cleaned do not stick (e.g., in corners of a square jar) or get caught (e.g., in a neck area connecting the body cavity to the lid) would be suitable. The cleaning beads may be of the same type as those suitable for use as polishing beads. In general, a mixture of cleaning beads of different sizes is preferred.

If the cleaning slurry does not contain alumina, the cleaning beads are preferably glass beads and are the same type as those described above for the polishing slurry, except that they are not conditioned to a slightly worn state. Although preconditioned glass beads will clean the polished surfaces, glass beads in their raw state are more effective in removing the frosty appearance from the polished articles. Raw glass beads received from commercial suppliers are preferably washed before being used in a cleaning slurry. An effective washing procedure involves sequentially tumbling the beads in acidic (e.g., 2N HCL for 10 minutes) and basic (1% NaOH for 1 hour) washing solutions, respectively. If the cleaning slurry comprises alumina polishing powder, the cleaning beads are preferably conditioned glass beads—the same type preferably used in the polishing slurry.

The necessary number and size distribution of cleaning beads will vary with the number and size of the articles to be polished, but a suitable selection can be easily determined without undue experimentation. In the case of the Preferred Acrylic Material, for example, the cleaning slurry added to a 1 liter receptacle would comprise approximately 1000 g of cleaning beads as follows: about 250 g of 0.5 mm glass beads and about 750 g of 1.0 mm glass beads (larger sizes of beads are generally avoided in an attempt to reduce the possibility that the cleaning beads will damage the surface of the articles).

If the cleaning slurry contains sodium hydroxide, the aqueous sodium hydroxide concentration in the cleaning slurry is preferably on the order of 0.5 to 1% (w/w). Greater concentrations of sodium hydroxide do not appear to provide any help in cleaning the articles; instead the higher concentrations just degrade the glass beads faster. At least some sodium hydroxide is necessary, however, because it seems to "soften" the cleaning; that is, it seems to help avoid damage to the articles' surfaces. In the absence of sodium hydroxide, the cleaning step may damage the surfaces of the articles such that they have an "orange-peel" appearance. Sodium hydroxide may be added to the cleaning slurry in the form of an undissolved solid or as an aqueous solution.

On the other hand, if the cleaning slurry contains alumina polishing powder, and a surfactant, suitable solvents are those in which the alumina is not soluble. In the most preferred embodiment, the polishing slurry contains a mineral spirits solvent having a flash point of about 90–145° F. as the swelling agent and the cleaning slurry contains the same solvent.

Suitable surfactants are those that dissolve in the chosen solvent and are capable of suspending the alumina particles in the solvent. The preferred amount of surfactant in the cleaning slurry is that amount which provides about a 1:1 ratio (w/w) with the amount of alumina in the cleaning slurry. Reducing the ratio of surfactant to alumina may allow the alumina particles to become imbedded in, or cause damage to, the surface of the articles being cleaned. Increasing the ratio of surfactant to alumina may reduce the effectiveness of the cleaning process. The preferred surfactant for use with stoddard solvent is dioctyl sulfosuccinate ("DSS"), a commercially available surfactant.

Alumina polishing powder is commercially available. The preferred amount and "mesh size" of the alumina will depend on other process parameters, including the identity of the soft acrylic material. Available mesh sizes of alumina range from less than 0.05 micron to 3.0 micron and larger. In general, however, the cleaning slurry contained in a 1 liter receptacle will require a minimum of approximately 0.25 % of alumina to solvent (w/w) to achieve acceptable cleaning results, regardless of the size and shape of the articles being cleaned. Increasing the amount of alumina and surfactant seems to increase the efficiency of the cleaning slurry, up to a maximum of about 1.50% (w/w of each alumina and surfactant). Higher concentrations may damage the articles being cleaned, and do not appear to significantly improve cleaning results. In the case of the Preferred Acrylic Material, the cleaning slurry contains 0.5% of 0.05 micron alumina, and 0.5% DSS to solvent (w/w).

The volume of liquid which should be included in the cleaning slurry depends upon the volume of cleaning beads, the number and size of the articles to be tumble-cleaned, etc. In general for tumble cleaning, however, the cleaning slurry should contain a liquid level sufficient to prevent the cleaning beads from becoming too dry and riding along the inside surface of the cleaning receptacle to the extent that they fall sporadically or too violently. Instead, the cleaning beads should tumble relatively smoothly. Likewise, the volume of liquid in the cleaning slurry should not be too great that the articles to be cleaned float or remain outside the stream of tumbling cleaning beads. For example, in the case of the Preferred Acrylic Material, a 1 liter receptacle containing 1000 g of glass cleaning beads as described above, will contain approximately 250 mL of liquid.

Unlike the polishing step, it is not necessary that the cleaning step be conducted at cryogenic temperatures. Instead, it is preferred that the cleaning step be conducted at a temperature sufficiently above the acrylic material's glass-transition temperature to insure that the article in cleaning slurry is soft and at least slightly flexible to aid in the removal of any frosty or hazy residue. In the case of the Preferred Acrylic Material, the cleaning step is preferably conducted at about 18° C. or higher.

As in the case of the polishing step, the optimal time and rotation speed for the cleaning step will vary with the batch size, identity of the soft acrylic material, the size and shape of the articles to be cleaned, the condition of the cleaning beads, etc. When the methods of the present invention are used to polish intraocular lenses, a typical batch size will be on the order of 50–100 lenses for a 1 liter receptacle. In the case of the Preferred Acrylic Material, excellent polishing results are obtained when the article is tumble-polished for approximately 1–4 days, with the rotation speed of the receptacle being approximately 80 rpm. After approximately 1–2 days of tumble cleaning using glass cleaning beads which have not been worn, intraocular lenses made of the Preferred Acrylic Material are very clean (no frosty appearance) and optically clear with no cosmetic blemishes.

Certain embodiments of the present invention are illustrated in the following examples.

EXAMPLE 1

TUMBLE POLISHING OF INTRAOCULAR LENSES (Preferred Acrylic Material)

A 1000 mL square Nalgene tumbling jar was filled with approximately 1000 g of a mixture of glass polishing beads. The mixture contained approximately 25% 0.5 mm, 50% 1.0 mm, and 25% 2.0 mm glass beads. To this was added 2.0 g of sodium bicarbonate powder and 250 mls of stoddard solvent (EM Scientific, Gibbstown, N.J.). The jar and its contents were placed on a modified 3BAR tumbler (Topline Mfg. Co.) which was placed inside a freezer. The tumbler was modified to enable the tumbler motor to remain outside the freezer and to connect to the tumbler bars via a drive shaft which passed through the wall of the freezer. The tumbling unit was switched on low speed (80 RPM), and the jar was tumbled for approximately 30 minutes at −10° C. to allow the contents to chill prior to adding one piece intraocular lenses made from Preferred Acrylic Material. After adding 27 lenses, the jar which was placed back into the freezer and tumbled for 24 hours. After tumbling, the jar was removed and its contents were poured into a No. 6 sieve to separate the lenses from the glass beads. The lenses were then cleaned to remove any solvent or polishing residue. Cleaning was accomplished by placing the lenses into holding fixtures which were in turn placed in an ultrasonic cleaning tank (model T-28, L&R Co., Kearney, N.J.) containing a solution comprised of ultrafiltered water, 2-butoxyethanol (approx. 0.8%), Micro® detergent (approx. 1.6%), and ammonium hydroxide (approx. 2.4%) for 5 minutes. They were then rinsed with deionized water in an ultrasonic cleaning tank for 5 minutes, and inspected at 16X for roundness and surface finish quality. They appeared highly polished. All machining lines had been removed and the optic edges and haptics were smooth and rounded.

EXAMPLE 2

TUMBLE CLEANING OF INTRAOCULAR LENSES POLISHED IN EXAMPLE 1

($NaOH/H_2O$ CLEANING SLURRY)

A 1000 mL round glass tumbling jar was filled with approximately 1000 g of a mixture of glass polishing beads. The mixture contained approximately 25% 0.5 mm and 75% 1.0 mm glass beads. To this was added about 250 mL of a 1% sodium hydroxide solution, and the tumble-polished soft acrylic lenses from Example 1. The jar was sealed and placed onto a 3BAR tumbler (Topline Mfg. Co.) in a temperature controlled environment maintained at approximately 25° C.±1° C. The jar and its contents were tumbled at 80 rpm for 48 hours. After tumbling, the jar was removed and its contents wee poured into a No. 6 sieve to separate the lenses from the glass beads. The lenses were rinsed briefly with deionized water and inspected at 16X for removal of the frosty coating. The lenses appeared clean and clear, with no traces of the frosty coating left on the surface by the tumble polishing operation.

Because no polishing agent is used in this step, a slightly rough bead surface is desired. As received from manufacturers, glass beads generally have a relatively rough surface. For other applications these beads often require extensive pre-conditioning before they can be used. The best results in the present application, however, have been obtained with glass beads that are in the nearly "raw" state (that is, glass beads that have been merely cleaned and not preconditioned). Cleaning the glass beads is performed by first tumbling the 'raw' beads in a 1% HCl solution at 80 rpm for 1 hour, after a brief deionized water rinse, they are tumbled for 24 hours in a 1% sodium hydroxide solution at 80 rpm. The beads are then thoroughly rinsed in deionized water and are ready for use. Over time, as the cleaning slurries are re-used, their effectiveness will gradually decrease and they will need to be replaced. The used tumble-cleaning beads, which are now considered preconditioned, are ideal for use in the tumble polishing operation.

EXAMPLE 3

TUMBLE POLISHING INTRAOCULAR LENSES (SECOND ACRYLIC MATERIAL)

The polishing and cleaning methods described in Examples 1 and 2 were followed, and 12 one-piece soft acrylic intraocular lenses (80 wt. % 2-phenylethyl acrylate, 15 wt. % 2-hydroxyethyl methacrylate, 3.2 wt. % 1,4-butanediol diacrylate and 1.8 wt. % O-methallyl Tinuvin P; initiated with 1.8 wt. % Perkadox 16) were cryo-tumbled (same conditions as Example 1) for 2 days. After polishing, the lenses were inspected for roundness and surface cosmetics. The lens edges were round and smooth, and the lens surfaces were free of damage. The lens surfaces did not appear "orange peeled." Compared to the lenses polished in Example 1, these lenses were as polished or even more polished. These lenses seemed to polish faster or more easily than those in Example 1. The lenses were then tumbled cleaned for 2 days and inspected for cleanliness and damage. The lenses were not completely cleaned as they contained a slight haze or frost, and the surface of the lenses showed a slight degree of pitting. Thus, the tumble cleaning-step may need to be optimized for use with the optic portion of optical lens products made of this material. However, the finish following the cleaning step was suitable for haptics, corneal inlays and intracapsular rings, for example.

EXAMPLE 4 (COMPARATIVE)

TUMBLE POLISHING INTRAOCULAR LENSES

The polishing method as described in Example 1 was repeated except that the polishing slurry contained 200 mls of a 50/50 mixture of water and ethanol as the solvent and about 600 mls of a mixture of 0.5 mm and 1.0 mm glass polishing beads in equal amounts. The polishing slurry contained no sodium bicarbonate. This experiment reproduced the polishing method of U.S. Pat. No. 5,133,159, except that in this case the 95:5 alcohol:water ratio was lowered to 50:50 because such high concentrations of alcohol caused the instant lens samples to become so brittle that they cracked and broke apart during tumbling. Six intraocular lenses (Preferred Acrylic Material) were added to the polishing slurry, cryo-tumbled (same conditions as in Example 1) for 9 days, and then examined for roundness and cosmetics. The lens samples were approximately 50% complete for roundness, but contained severe surface scratching and pitting.

EXAMPLE 5 (COMPARATIVE)

TUMBLE POLISHING INTRAOCULAR LENSES

The polishing method as described in Example 1 was repeated using a polishing slurry containing a 50/50 mixture of water and ethanol as the solvent and 2.5 grams of sodium bicarbonate. This experiment reproduced the polishing method of U.S. Pat. No. 5,133,159, except that in this case not only was the 95:5 alcohol:water ratio lowered to 50:50 for the reason mentioned in Example 4 above, but sodium bicarbonate was added to the slurry in an attempt to improve the polishing results. Ten intraocular lenses (Preferred Acrylic Material) were cryo-tumbled (same conditions as in Example 1) for 8 days and then examined for roundness and cosmetics. Approximately 75% roundness had been achieved, but the lenses had severely "orange peeled" surfaces.

EXAMPLE 6

TUMBLE POLISHING OF INTRAOCULAR LENSES

The polishing method as described in example 1 was repeated with the exception that the polishing slurry contained 0.7 grams of sodium bicarbonate. Thirty-six intraocular lenses (Preferred Acrylic Material) were cryo-tumbled (same conditions as Example 1) for 2 days. At the conclusion of the polishing cycle, the jars contents were poured into a No. 6 sieve to separate the lenses from the polishing beads. The lenses were then inspected for machining and tool mark removal, as well as lens cosmetics. The polished lenses appeared typical of product seen at this stage in the process, the edges were smooth and polished, the corners were rounded, and the lens surfaces appeared slightly frosty.

EXAMPLE 7

TUMBLE CLEANING OF INTRAOCULAR LENSES POLISHED IN EXAMPLE 6

(Solvent-based Cleaning Slurry)

A 1000 ml round glass jar was filled with approximately 1000 g of a mixture glass cleaning beads. The mixture contained approximately 25% 0.5 mm and 75% 1.0 mm glass beads. To this was added approximately 1.0 g of 0.05 mesh size alumina polish, and 1.0 g of dioctyl sulfosuccinate (DSS). Finally, about 250 ml of stoddard solvent was added to the jar to complete the cleaning slurry mixture. The polished lenses from example 6 were then added to the cleaning jar, which was sealed and placed onto the 3BAR tumbler (Topline Mfg. Co.). The jar and its content were tumbled at 80 r.p.m. for approximately 24 hours at room temperature (23.8° C.). At the conclusion of the cleaning cycle, the jar was removed from the tumbler and its contents poured into a No. 6 sieve to separate the lenses from the cleaning beads. The lenses were rinsed briefly with deionized water and allowed to air dry before being inspected at 16X to determine whether the frosty coating was successfully removed. The lenses appeared clean and clear, with no trace of the frosty coating.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of polishing an article comprising a soft acrylic material, wherein the method comprises
    a) polishing the article by charging a receptacle with a polishing slurry and the article to be polished, and agitating the receptacle at a temperature no higher than about 0° C. for a period of time and at a speed sufficient to remove surface irregularities from the article, wherein the polishing slurry comprises polishing beads, sodium bicarbonate, and a swelling agent; and b) cleaning the article by charging a receptacle with a cleaning slurry and the article to be cleaned, and agitating the receptacle for a period of time and at a speed sufficient to clean the surface of the article, wherein the cleaning slurry comprises cleaning beads, sodium hydroxide, and water.

2. The method of claim 1 wherein the polishing beads and the cleaning beads are glass beads.

3. The method of claim 2 wherein the polishing beads comprise 0.5 mm, 1 mm and 2 mm glass beads in a 1:2:1 ratio.

4. The method of claim 2 wherein the cleaning slurry comprises 0.5 mm and 1 mm glass beads in a 1:3 ratio, and sodium hydroxide at a concentration of at least about 0.5% (w/w).

5. The method of claim 1 wherein the amount of sodium bicarbonate in the polishing slurry is at least 0.2% (sodium bicarbonate to swelling agent, w/w).

6. The method of claim 1 wherein the swelling agent is a solvent selected from the group consisting of alcohols; aliphatic hydrocarbons; chlorinated solvents; and aromatic hydrocarbons.

7. The method of claim 6 wherein the solvent is a mineral spirits solvent having a flash point of about 90–145° F.

8. The method of claim 1 wherein the swelling agent is a polymer solution capable of being imbibed into the soft acrylic material of the article to be polished, but which can be removed by a solvent extraction process.

9. The method of claim 1 wherein the article is selected from the group consisting of one-piece intraocular lenses, intraocular lens haptics, intraocular lens optics, intracapsular rings, corneal inlays, intracorneal lenses, and contact lenses.

10. A method of polishing an article comprising a soft acrylic material, wherein the method comprises a) polishing the article by charging a receptacle with a polishing slurry and the article to be polished, and agitating the receptacle at a temperature no higher than about 0° C. for a period of time and at a speed sufficient to remove surface irregularities from the article, wherein the polishing slurry comprises polishing beads, sodium bicarbonate, and a swelling agent; and b) cleaning the article by charging a receptacle with a cleaning slurry and the article to be cleaned, and agitating the receptacle for a period of time and at a speed sufficient to clean the surface of the article, wherein the cleaning slurry comprises cleaning beads, alumina, a surfactant and a solvent.

11. The method of claim 10 wherein the polishing beads and the cleaning beads are glass beads.

12. The method of claim 10 wherein the polishing beads comprise 0.5 mm, 1 mm and 2 mm glass beads in a 1:2:1 ratio.

13. The method of claim 10 wherein the amount of sodium bicarbonate in the polishing slurry is at least 0.2% (sodium bicarbonate to swelling agent, w/w).

14. The method of claim 10 wherein the ratio of alumina to surfactant concentration in the cleaning slurry is about 1:1 (w/w).

15. The method of claim 10 wherein the swelling agent is a solvent selected from the group consisting of alcohols; aliphatic hydrocarbons; chlorinated solvents; and aromatic hydrocarbons.

16. The method of claim 10 wherein the swelling agent in the polishing slurry and the solvent in the cleaning slurry are a mineral spirits solvent having a flash point of about 90–145° F.

17. The method of claim 10 wherein the cleaning slurry comprises from about 0.25–1.5% alumina (alumina to solvent, w/w).

18. The method of claim 10 wherein the article is selected from the group consisting of one-piece intraocular lenses, intraocular lens haptics, intraocular lens optics, intracapsular rings, corneal inlays, intracorneal lenses, and contact lenses.

* * * * *